United States Patent [19]

Baum et al.

[11] Patent Number: 4,989,590
[45] Date of Patent: Feb. 5, 1991

[54] IRRIGATION APPLIANCE

[75] Inventors: John Baum; Gary Thomas; James Hickman, all of Fort Collins, Colo.

[73] Assignee: Teledyne Industries, Inc., Fort Collins, Colo.

[21] Appl. No.: 541,549

[22] Filed: Jun. 21, 1990

Related U.S. Application Data

[63] Continuation of Ser. No. 875,203, Jun. 17, 1986, abandoned.

[51] Int. Cl.⁵ .................. A61H 9/00; A61G 17/02
[52] U.S. Cl. ........................... 128/66; 137/493.3; 137/493.8; 137/846; 251/149.1
[58] Field of Search ............... 128/66; 433/80, 84, 433/85; 137/493, 493.3, 493.6, 493.8, 493.9, 512.15, 846, 903; 251/149.1, 149.6; 222/318

[56] References Cited

U.S. PATENT DOCUMENTS

| Re. 27,274 | 1/1972 | Mattingly | 128/66 |
|---|---|---|---|
| 1,933,454 | 10/1933 | Sidney | 137/493.3 |
| 3,209,956 | 10/1965 | McKenzie | 222/318 |
| 3,216,619 | 11/1965 | Richards et al. | 222/318 |
| 3,227,158 | 1/1966 | Mattingly | 128/66 |
| 3,501,203 | 3/1970 | Falk | 137/493.6 |
| 3,590,813 | 7/1971 | Roszyk | 128/66 |
| 4,001,526 | 1/1977 | Olson | 200/153 J |
| 4,108,167 | 8/1978 | Hickman et al. | 128/66 |
| 4,109,650 | 8/1978 | Peclard | 128/66 |
| 4,302,186 | 11/1981 | Cammack et al. | 433/80 |
| 4,382,167 | 5/1983 | Maruyama et al. | 200/153 J |
| 4,442,831 | 4/1984 | Trenary | 128/66 |

FOREIGN PATENT DOCUMENTS

655237 4/1987 Switzerland ................ 128/66

Primary Examiner—John J. Wilson
Attorney, Agent, or Firm—Hugh H. Drake

[57] ABSTRACT

An irrigation appliance uses a reservoir which inverts to form a cover and includes a simplified valve in the reservoir as well as a switching mechanism adapted thereto. Liquid delivered to the unit from the reservoir is controlled as to pressure by adjustment on a hand-held device remote from the unit. In the base unit are elements which regulate forward and backward flow in order to obtain outlet pressure control.

28 Claims, 4 Drawing Sheets

IRRIGATION APPLIANCE

The present application is a continuation of co-pending application Ser. No. 07/875,203 filed June 17, 1986, now abandoned.

This application relates to subject matter of special concern to irrigation appliances. More particularly, it relates to improvements in connection with apparatus within this general field.

The most pertinent background is probably that contained in the field of oral hygiene appliances, although it has been recognized that many of the improvements in appliances for that field also find useful application in other areas such as the medical cleaning of wounds or cavities. Representative of the prior art are U.S. Pat. Nos. 3,227,158, 3,425,410, 3,453,969, 3,467,083, Re 27,274, 4,094,311, 4,108,167, 4,302,186, 4,442,831, 4,452,238 and 4,534,340, as well as some of the patents cited therein.

All of the foregoing patents involve the delivery of water in pulses with a degree of control of some characteristic such as pressure. Usually, pressure control was included in the base unit. As will be observed, there have been some suggestions of placing it in the user's handpiece, so that the user could achieve that control without removing the handpiece from his mouth when it was still delivering liquid. An alternative was to employ a second hand in an inconvenient manner while at the same time collating coordination.

Also included in the development within this general field was that of more and more convenient and often portable units which enabled either or both of easy transportation or attractive storage on such as a bathroom counter top. One early approach was that described in above U.S. Pat. No. Re 27,274 which adopted the inverted reservoir that, when placed downwardly, served as a cover.

Thus, there have been many improvements in this art at the same time that a few stones have been left unturned. It is a general object of the present invention to overturn a few more of those stones and achieve further improvements in this art.

One further object of the present invention is to provide a new and improved cover assembly which better accommodates storage of everything when the unit is not in use and yet which facilitates use during operation.

Another object is to provide better electrical operational facilities for the kind of unit in question.

A still further object is to afford the user with a greater degree of convenience in control of the pressure of delivered irrigating water or other liquid.

In one aspect, the appliance includes a housing having top and bottom walls joined by circumferential side walls shaped to define an inset, along a portion thereof, that mates with a cover having a normally horizontal wall from which projects a circumscribing wall shaped to mate and has a similar inset. A platform on the housing projects outwardly so that there is a seat which enables an outlet device to be so positioned that it is readily available to the user.

Another aspect of the present invention involves a new valve for use between such an inverted reservoir in the form of a cover and its housing. That valve features an I-shaped structure all of resilient material. Structure formed in the housing may open the valve, but cooperating structure in the cover lets the valve prevent drainage when the inverted cover is removed.

Still another aspect of the new invention is the inclusion of a switch arrangement so arranged in this environment that it enables push-push switching while yet having hermetic sealing, so as to protect the interior. This involves the use of a well disposed in the housing and into which a barrel is inserted that carries cooperative switch contacts. That barrel is tied to an operator assembly which enables push-push operation.

One leading feature of that which is claimed, however, pertains to that which might be called remote control of pressure adjustment. The remote control is a simple valve located in the hand-held device that allows complete pressure control. This involves a system within the base unit which modulates flow from the reservoir to the pumping unit and to the hand-held device in response to the valve on that device, while at the same time modulating reverse flow back to the reservoir from the pumping unit when the pressure or flow rate of delivery is reduced by adjustment at the hand-held unit.

The features of the present invention which are believed to be patentable are set forth with particularity in the appended claims. The organization and manner of operation of one or more specific embodiments of the invention, together with further objects and advantages thereof, may best be understood by reference to the following description taken in connection with the accompanying drawings, in the several figures of which like reference numerals identify like elements, and in which:

Figure 1:
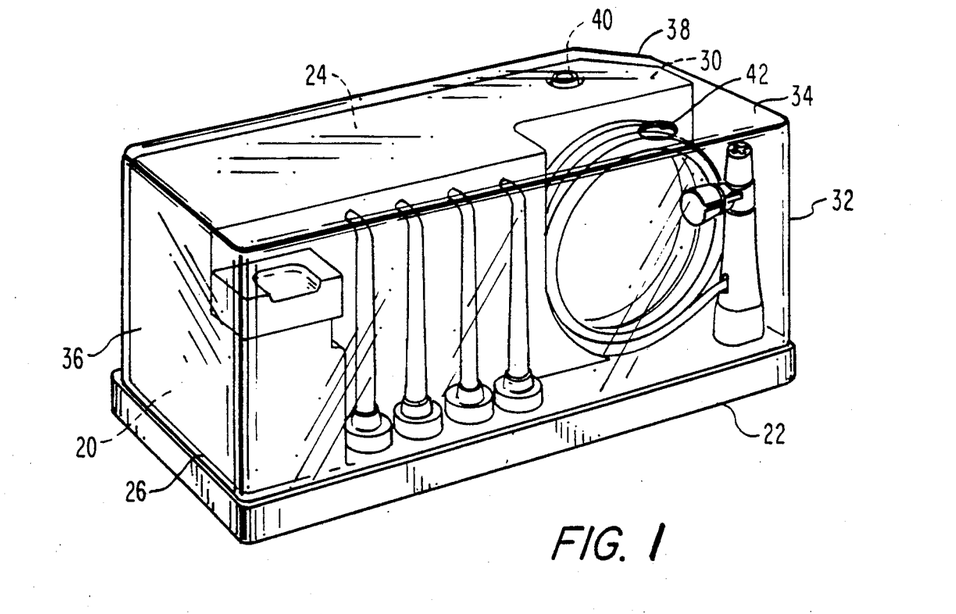
FIG. 1 is a perspective view of an irrigation appliance constructed in accordance with the present invention.

Shown in FIG. 1 is an irrigating appliance specifically originated for use in the field of oral hygiene. It enables the user to direct a pulsating jet of water or other liquid for the purpose of tooth cleaning and gum massage. However, such units also have found important use in other areas at least in personal care for such different implementations of use as wound debridiment or the flushing of debris from a cavity. The overall operation of this kind of apparatus is well described in various ones of the patents mentioned in the introduction to this application, and those patents are incorporated herein by reference for detailed understanding of constructional details which may be employed.

The unit depicted in FIG. 1 includes a housing 20 secured atop a base 22 and within which housing are disposed certain operative components later to be described. Housing 20 has a top wall 24 and an upper surface on base 22 serves as a bottom wall 26. Top wall 24 and bottom wall 26 are joined by a circumferential side wall 28 shaped to define an inset 30 displaced laterally to and formed at a corner location along one portion of sidewall 28.

A cover 32 has a normally horizontal wall 34 from which laterally projects a circumscribing wall 36 shaped to mate with side wall 28 when cover 32 is positioned to overlie housing 20 in enveloping relationship. Wall 36 also has an inset 38, displaced laterally to and formed at a corner location along circumscribing wall 36, that mates with inset 30 when cover 32 is so positioned.

Figure 2:
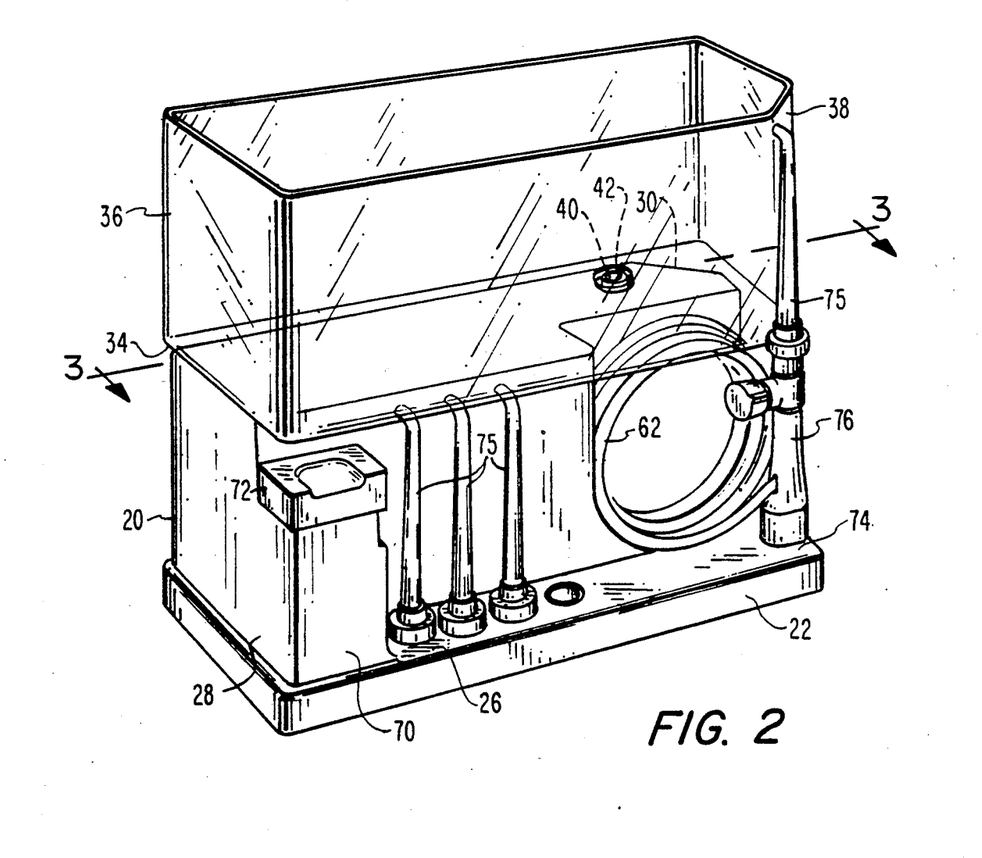
FIG. 2 is a similar view with different components arranged in different positions.

An inlet 40 is formed in top wall 24. An outlet 42 is formed to define an opening through horizontal wall 34 and is so located as to be aligned with inlet 40 when cover 32 is inverted to dispose its circumscribing wall 36 normally upstanding from top wall 24. As indicated, circumscribing wall 36 is shaped to mate with side wall 28 when cover 32 is positioned to overlie the housing in enveloping relationship, with inset 38 mating with inset 30 when cover 36 is so positioned.

Figure 3:
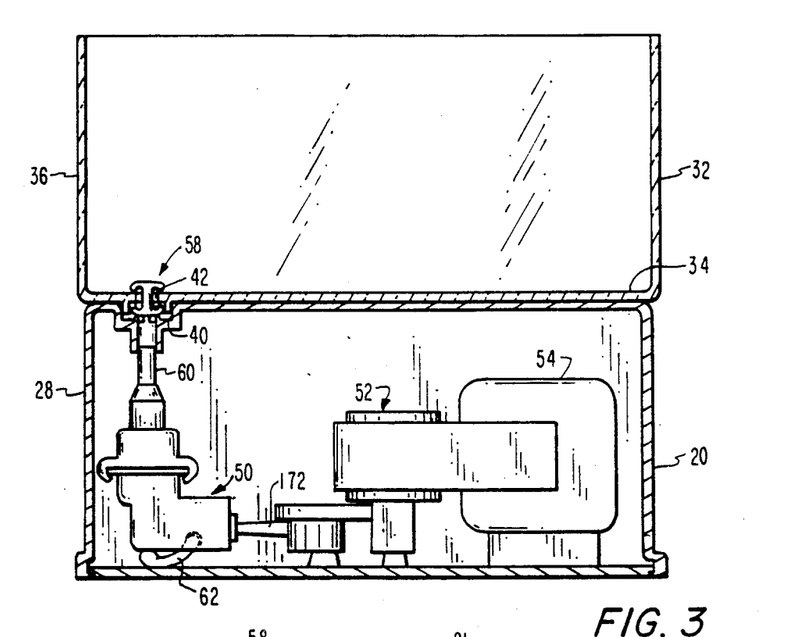
FIG. 3 is a cross-sectional view taken along the line 3—3 in FIG. 2.

Disposed within housing 20 is a pump 50 driven through a motion converter 52 from an electric motor 54. Broadly viewed, such a pumping assembly may take the form shown in the aforementioned U.S. Pat. No. 4,302,186. Alternatively, the overall pumping assembly may be constructed with a different approach, such as the solenoid pump shown in application Ser. No. 648,766 filed Sept. 10, 1984, now U.S. Pat. No. 4,607,627.

In any event, liquid contained within the reservoir of cover 32, when disposed in its exposed upright position as shown in FIG. 2, is suctioned through a valve 58, which is displaced upwardly in the bottom of cover 32 at outlet 40, and through input tubing 60 into the pump body from which said liquid is delivered under pressure through an outlet hose 62 that continues outwardly of housing 36. Again speaking broadly, this overall arrangement was described in more detail in U.S. Pat. No. Re 27,274.

What in use normally would be the front or user's side of the appliance features an upstanding pedestal 70 located in this case to one side and which contains a switching mechanism operated by a push button 72. Further along the front the upper surface of base 22 projects fixedly outward from housing 20 to serve as a platform 74 along which are defined a plurality of wells to accept the seating of a corresponding plurality of jet tips 75. Jet tips 75 may be as described in more detail in U.S. Pat. No. 4,337,040.

An indentation in housing 20, disposed inwardly from platform 74, accepts a multi-turn coil of outlet conduit 62 which leads to a handpiece 76 seatable for storage within another well formed in platform 74 or, alternatively, might seat upon a peg upstanding from that platform.

As shown in FIG. 1, when cover 32 is downturned so as to cover the entire unit, it embraces both tips 75 and handpiece 76. On the other hand, when cover 32 is inverted so as to serve as a reservoir for a liquid, inset 38 exposes handpiece 76 and an attached jet tip 75 for grasping and use by the operator.

Figures 4, 5, 6:
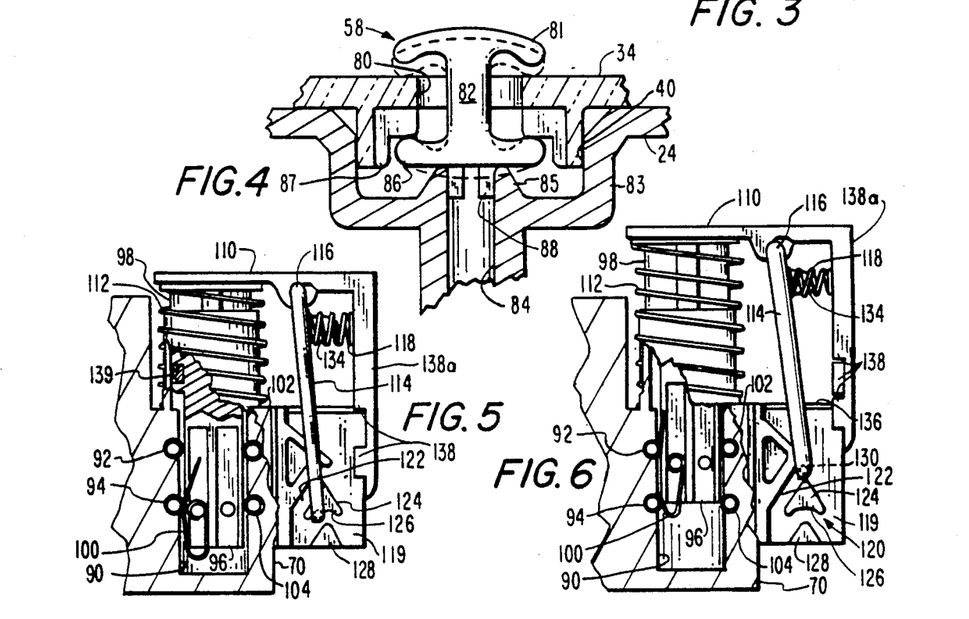
FIG. 4 is a fragmentary cross-sectional view of a component shown in FIG. 3.
FIGS. 5 and 6 are cross-sectional views of a subassembly included in FIGS. 1 and 2 and respectively showing individually different components in different positions.

In this case, valve 58 preferably is constructed as shown in FIG. 4, although it alternatively may take a different form such as that shown in several of the references previously mentioned. Here, valve 58 is generally of an I-shape and is composed of a resilient material. It is disposed within an opening 80 formed in horizontal wall 34. Its transverse upper bar 81 at one end of a leg 82 seals opening 80 when it is disposed downwardly by resilient bar 86. A well 83 defined in top wall 24 has a centrally located passage 84. A circular nub 85 projects upwardly within well 83 to a location at which it engages the bottom surface of a lower transverse bar 86.

Thus, when cover 32 is removed from the base, valve 58 moves downwardly into sealing relationship against horizontal wall 34. But when cover 32 is inverted and placed atop wall 24 in order to serve as the reservoir, nub 85 urges valve 58 upwardly, allowing flow of liquid from the reservoir through opening 80 and downwardly past a circumferentially spaced series of flutes 87 projecting from wall 34 and with the liquid then flowing through the interstices between those flutes on into passage 84 through additional flutes 88.

Defined within pedestal 70 is a well 90. Exposed through the wall of well 90 are a pair of electrical contacts 92 and 94 which are spaced apart longitudinally of the well. A barrel 96 is slideably disposed within well 90 and has one end portion 98 projecting outwardly from well 90. An elongated and resilient electrically-conductive element 100 is secured on the lower end portion of barrel 96 in alignment with contacts 92 and 94. Element 100 is of a conformation, as shown, to electrically bridge contacts 92 and 94 when barrel 96 is moved to a first position upwardly as shown in FIG. 6, yet to open that bridge when barrel 96 is moved to a second and lower position as shown in FIG. 5.

The switch assembly being described may also include a second longitudinally-spaced pair of contacts 102 and 104, enabling the switch to serve in a single-throw, double-pole configuration whenever it may be desired to separately switch the supply of power not only to motor 54 but also to other apparatus. The latter might be a microprocessing unit as may be desirable when incorporating a different kind of pump as for instance in the case of the aforementioned solenoid pump.

An operator 110 is secured to the upper end portion 98 of barrel 96. A spring 112 is disposed with respect to barrel 96 to urge the barrel to an upper position but is yieldable in response to pressure exerted on operator 110 in order to move the barrel into the second and lower position. A finger 114 is pivotably connected at one end 116 by an inward-facing lug 117 which seats in a recess formed in the side of operator 110 in order to enable finger 114 to swing laterally. A second spring 118 is disposed with respect to operator 110 in order to urge finger 114 to swing in a first direction to the left as shown in FIGS. 5 and 6.

Also defined in pedestal 70 on an outwardly-projecting wall 119 is a raceway generally indicated at 120 and including a first ramp 122 and a second ramp 124, both together with the formation on wall 119 of a notch 126 spaced above a directing nub 128. A pin 130 projects inwardly from the lower end of finger 114 into raceway 120, enabling travel of pin 130 out of notch 126 into ramp 122 under urging of spring 118 upon the application of pressure to operator 110 followed by movement of barrel 96 outwardly of well 90 under urging of spring 112. Subsequently, and upon renewed pressure applied to operator 110, pin 130 is caused to travel along ramp 124 as a result of which, under the urging of spring 118, pin 130 is caused by the additional ramping presented by director 128 to return into notch 126.

Preferably, the opposite side of wall 119 (not shown) carries a mirror image of raceway 120, notch 126 and nub 128. Finger 114 then is joined by a bridge 132 (FIG. 6A) to a counterpart finger 114' having a lug 117' and a pin 130'. A post 134 on bridge 132 seats in and holds spring 118 in position. This balanced arrangement improves stability of the assembly, and bridge 132 holds fingers 114 and 114' together. This permits lugs 117 and 117' as well as pins 130 and 130' to be sprung apart and then snapped into their respective recesses and raceways.

Figures 6A, 10, 11, 12:
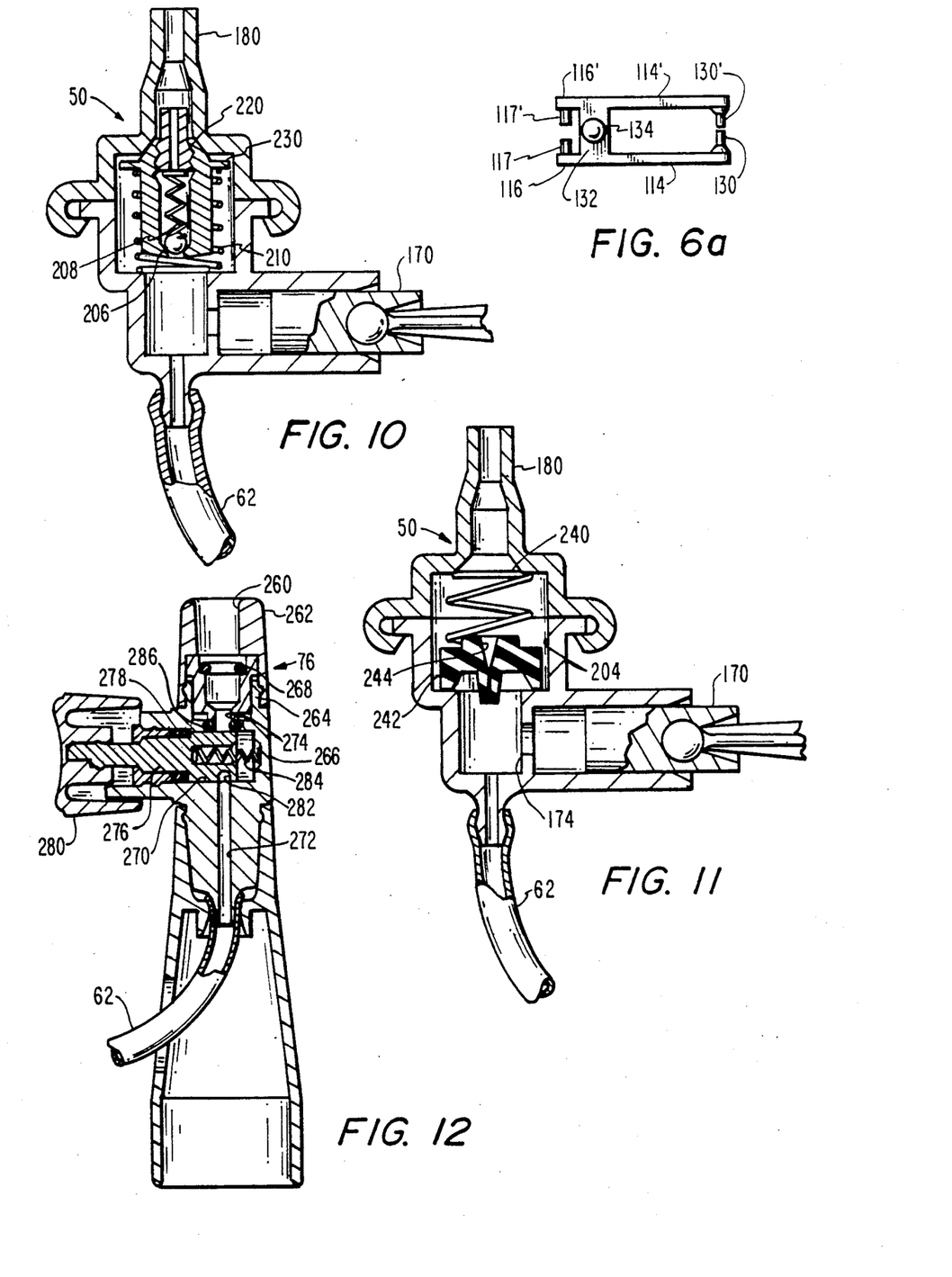
FIG. 6A is a side elevational view of a component shown in FIGS. 5 and 6.
FIGS. 8, 9, 10 and 11 are longitudinally-taken cross-sectional views of a component included in FIG. 3 but individually showing respective different specific approaches.
FIG. 12 is a cross-sectional view of an alternative to the component shown in FIG. 7.

The upper edge of wall 119 tapers to a point at 136 to assist in spreading pins 130 and 130' during assembly. Also aiding stability, ears 138 project inwardly from skirt 138a of operator 110 to ride on respective sides of wall 119.

It will thus be seen that a so-called push-push switch has been formed. It is bistable, switching from one mode to the other mode on each successive actuation of operator 110. An important additional feature shown in FIG. 5 is the inclusion of an hermetic seal 139 seated between barrel 96 and the upper end portion of well 90. Considering that use of the appliance as specifically embodied is intended to be performed within an environment which often includes at least a high degree of humidity, if not the inadvertent splashing of liquid such as water on the unit itself, seal 139 assists in avoiding moisture-related problems in the performance of the switching mechanism.

Figures 7, 8, 9:
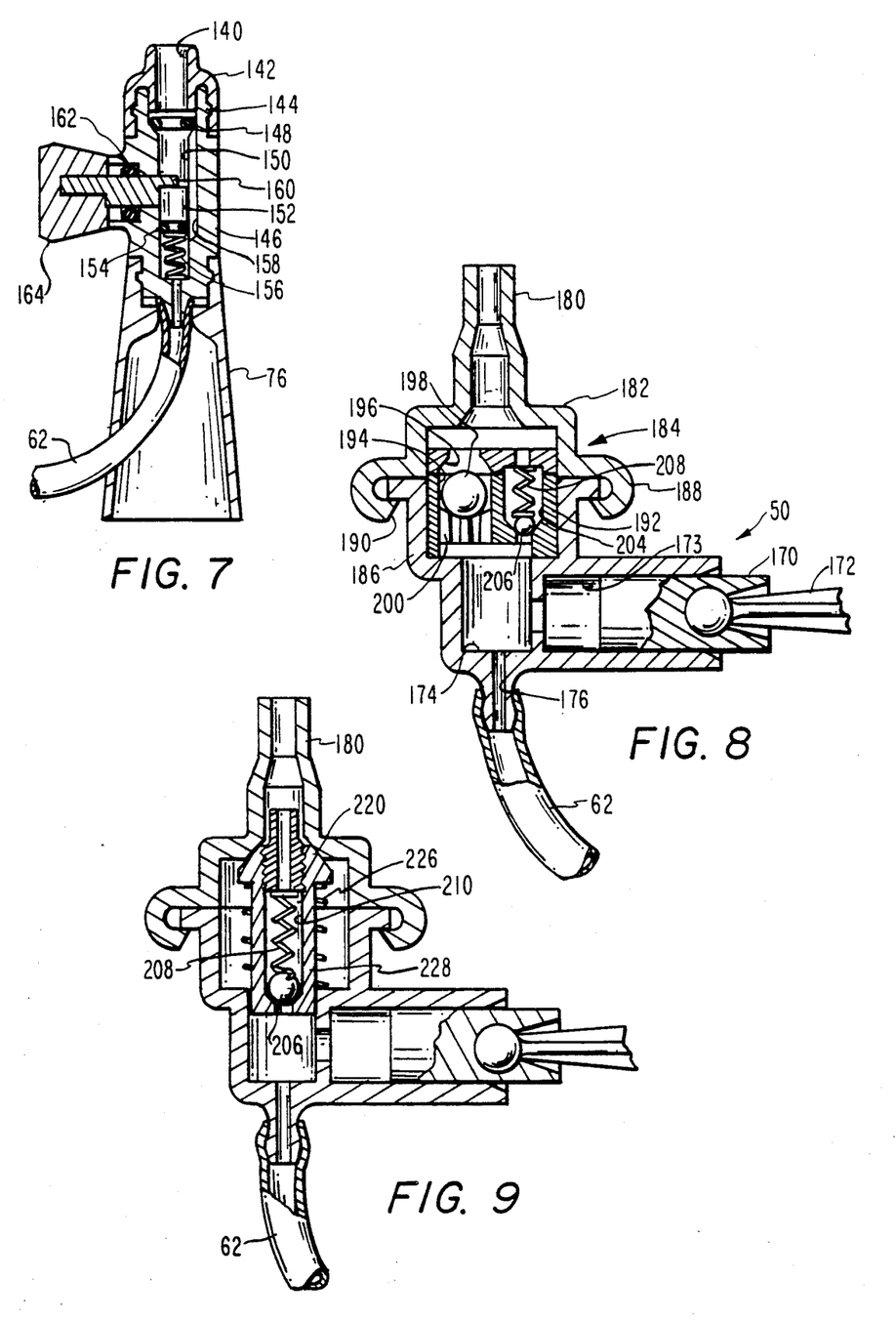
FIG. 7 is a cross-sectional view taken longitudinally through a component shown in FIGS. 1 and 2.

Handle 76 is located at the outer end of flexible hose 62 and includes a seat 140 receptive of the lower end of jet tip or nozzle assembly 75. As shown in FIG. 7, seat 140 is defined within a cap 142 which may be snap fitted upon a nose 144 of a cylinder 146. An O-ring 148, disposed within nose 144, accommodates the very lower end of jet tip 75 in the manner described in the aforementioned U.S. Pat. No. 4,302,186.

Within a bore 150 of cylinder 146 is a plunger 152 at the base of which is an O-ring 154 and which is urged in an upward direction, as shown, by a spring 156. Defined at one side of bore 150 is a channel 158 the lower end of which may be variably opened in correspondence with the vertical position of plunger 152. Channel 158 allows flow around plunger 152 and on into the upper end of bore 150 for delivery by tip 75. That is, hose 62 is coupled into the bottom of bore 150 to enable liquid flow through and around spring 156 and into channel 158.

Adjusting longitudinal position within bore 150 of plunger 152 is a tab 160 which projects over the upper end of plunger 152 and is secured through an O-ring 162 to a finger-operable knob 164. As will now be evident, rotation of knob 164 about its own longitudinal axis causes movement of plunger 152 relative to channel 158 in order to throttle the rate of flow of liquid arriving by way of hose 62 and ultimately delivered through a tip 75.

Pump 50 is shown in all of FIGS. 8-11 in presently preferred forms, although, as indicated above, it may take other forms. In FIG. 8, it includes a piston 170 moved by a connecting rod 172 driven as usual through converter 52. Piston 170 slides within a cylinder 173 reciprocally in order to develop alternate pressure and suction within a manifold 174. The outlet 176 from manifold 174 is coupled into flexible hose 62. As such, piston 170 and its joinder to rod 172 preferably are constructed in accordance with the teaching in U.S. Pat. No. 4,108,167.

Passage 84 within the housing assembly of FIG. 4 is coupled into a snout 180 which leads into an upper cap 182 as part of a housing within which is defined a governor 184. Cap 182 mates with a lower portion 186 in this case integrally formed with and upstanding from the main pump body and in communication with manifold 174. As shown, cap 182 has a flange 188 which carries a tapered surface 190 so formed as to enable a snap fit of cap 182 upon body 186.

Seated within body 186 and partially within cap 182 is an insert 192 within which is defined a first channel 194 narrowed down at its upper end 196 in order to seat a ball valve 198 when the latter is urged upwardly by the development of pressure within manifold 174. Below valve 198 are ribs 200 which allow valve 198 to be limited in movement while yet allowing liquid from reservoir 34 to be drawn into manifold 174 upon the suction stroke of piston 170 and thereafter forced into hose 62 during a subsequent pressure stroke at which time valve 198 is sealed at 196. Thus, valve 198 serves as a free-floating inlet check valve, otherwise functioning in the same manner as that which is described in several of the prior patents herein above mentioned.

Another channel 204 leads from the inlet to the outlet side through insert 192 and is necked down at its lower end, adjacent to manifold 174, so as to define a seat for a ball valve 206 urged downwardly by a spring 208. Ball valve 198 serves as a first regulator that responds to pump suction for enabling liquid flow from reservoir 34 at a rate determined in response to adjustment of the throttling action within remote and physically-separated hand-held device 76, in this case by means of mere finger-operable twisting of knob 164. At the same time, ball valve 206 and its associated components serve as a second regulator responsive to pressure developed by piston 170 to enable liquid flow back from manifold 174 into reservoir 34 at a rate correspondingly determined by that same throttling adjustment accomplished within the remote hand-piece. Thus, the two check valves are reciprocally poled to pass liquid in opposing directions to and from the reservoir, but the action is coordinated with throttling control at the remote hand-piece.

FIGS. 9 through 11 illustrate alternatives devised for accomplishing the same results of governing liquid flow in response to throttling action. In FIG. 9, ball valve 206 urged by spring 208 is located within an internal bore 210. Ball valve 198 of FIG. 8 is in this case replaced by a truncated nose 220 urged upwardly by a spring 226. That latter combination serves the purpose of ball valve 198 as explained with regard to that shown in FIG. 8. When the valve established at 220 is caused to move downwardly by pump suction, the liquid flows from the reservoir through a space left, or fluting provided in, the lower end of the drum-shaped structure 228 of valve 220.

The alternative depicted in FIG. 10 is similar to that of FIG. 9, in that valve 206 is loaded by a spring 208 again within an internal bore with an upper valve 220 serving as the inlet check valve. The primary difference here is that the liquid flows around a pair of flanges 230 formed on body 220, possibly eliminating alignment problems that might occur with the arrangement of the version of FIG. 9.

The different versions of FIGS. 8-10 have all used ball-type check valves. As FIG. 11 illustrates, that is not a necessary limitation in terms of freedom of design. In this case, disposed within cavity 204 is only a single spring 240 that downwardly urges a multiple-valve body 242 which seats around the entrance to manifold 174 in order to serve, along with spring 240, as the reverse-flow regulator. At the same time, body 242 includes an internal passage 244 which opens in response to suction produced by piston 170. Thus, and as shown, body 242 becomes both the first regulator and the second regulator, with respect to alternative directions of liquid flow to or from reservoir 34. Internal opening 244 permits unidirectional flow as a part of a second check valve, the second check valve actually being formed by the upward movement, against spring 240, of body 242 upon increase in pressure within manifold 174 in response to throttling action by adjustment of knob 164 in the remote hand-piece.

FIG. 12 illustrates an alternative user-held handle 76' which is similar to handle 76 as shown in detail in FIG. 7 but which presently is preferred since it affords an additional feature. Handle 76' again is located at the outer end of flexible hose 62 and includes a seat 260 receptive of the lower end of jet tip or nozzle assembly 75. Seat 260 is defined within a cap 262 snap fitted upon a nose 264 of a cylinder 266. An O-ring 268, disposed within 264, accommodates the lower end portion of tip 75 as before.

Contained within bore 270, oriented laterally of cylinder 266 and continuing across an inlet passageway 272 aligned with an outlet passageway 274, is a cylindrical valve 276. Valve 276 is sealed within bore 270 by an O-ring 278. A knob 280 is mounted on the projecting outer end of valve 276. Defined circumferentially in the exterior surface of valve 276 is a channel 282 the depth of which changes in a direction around the circumference of valve 276. Valve 276 is urged outwardly of cylinder 266 by a compression spring 284. A seal 286 confines flow from channel 282 into passageway 274.

In its normal outward position, channel 282 is aligned between passages 272 and 274, with the latter being sealed to the exterior surface of valve 276 by an O-ring 286. In the position illustrated, rotation of valve 276, by means of knob 280, changes the depth of channel 282 presented for the flow of water from passage 272 on upwardly to passage 274. On the other hand, mere thumb or finger pressure by the user on the outer end of knob 280 urges valve 276 inwardly against the force of spring 284 thereby displacing channel 282 out of the flow passageway and completely shutting out the flow of liquid. This enables the user to immediately shut off the delivery of water from the nozzle with a simple pushing motion of, say, his thumb. That allows the user to remove the nozzle from his mouth and either direct it into a basin and/or reach down with a digit of either hand and turn off the appliance so as to stop operation altogether.

It will thus be seen that a number of advantageous features have been incorporated into a new appliance specifically designed for oral irrigation but also readily adaptable for other types of irrigation in connection with both personal and other use. At the same time, different features have been revealed that lead to convenience of user operation. Also disclosed have been a variety of different features believed to be useful in and of themselves.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of that which is patentable:

We claim:

1. An irrigation appliance comprising:

a housing having a top wall and a bottom wall joined to said top wall by a circumferential side wall shaped to define an inset displaced laterally to and formed along one portion thereof;

a cover having a normally horizontal wall from which laterally projects a circumscribing wall shaped to mate with said side wall when said cover is positioned to overlie said housing in enveloping relationship, said circumscribing wall also having an inset, displaced laterally to and formed along said circumscribing wall, that mates with said inset of said side wall when said cover is so positioned;

inlet means defining an opening in said top wall;

outlet means defining an opening in said horizontal wall and so located as to be aligned with said inlet means when said cover is inverted to disposed said circumscribing wall normally upstanding from said horizontal wall;

means disposed within said housing for outletting a liquid therefrom;

means disposed within said housing for pumping liquid from said inlet means to said outletting means;

a device coupled for liquid flow from said outletting means for delivery to a point of use;

said bottom wall of said housing having a platform portion which fixedly projects outwardly from beneath said inset in said cover when said cover is so inverted;

and means in said platform portion defining a seat for exposure of said device adjacent to said inset when said cover is so inverted.

2. An irrigation appliance as defined in claim 1 in which said platform portion is so located that at least a portion of said device is enabled to be enclosed within said cover when said cover is disposed in said enveloping relationship.

3. An irrigation appliance as defined in claim 1 in which said device includes a selected one of a plurality of nozzles and in which another portion of said platform includes receptors for storing different ones of said nozzles at a location within said cover when said cover is in said enveloping relationship but which are exposed when said cover is so inverted.

4. An irrigation appliance as defined in claim 1 in which said insets are located at respective corners of said side wall and said circumscribing wall.

5. An irrigation appliance comprising:

a housing having a top wall and a bottom wall joined to said top wall by a circumferential side wall;

a cover having a normally horizontal wall from which laterally projects a circumscribing wall shaped to mate with said side wall when said cover is positioned to overlie said housing in enveloping relationship;

inlet means defining an opening in said top wall;

outlet means defining an opening in said horizontal wall and so located as to be in alignment with said inlet means when said cover is inverted to dispose said circumscribing wall normally upstanding from said horizontal wall;

a generally I-shaped valve composed of resilient material and disposed with its leg within said opening in said horizontal wall, said valve having a transverse bar at one end of said leg that seals said opening in said horizontal wall when urged downwardly in normal use;

means disposed within said inlet opening for engaging another transverse bar at the other end of said leg and urging said valve in a direction disengaging the sealing of said opening;

and outletting means coupled to said housing for delivering liquid from said inlet to a point of use when said valve is opened.

6. An irrigation appliance comprising:

a housing having a top wall and a bottom wall joined to said top wall by a circumferential side wall;

a cover having a normally horizontal wall from which laterally projects a circumscribing wall shaped to mate with said side wall when said cover is positioned to overlie said housing in enveloping relationship;

means for permitting liquid stored in said cover, when inverted to dispose said circumscribing wall normally upstanding from said horizontal wall, to flow into said housing;

means defined in said housing for outletting said liquid therefrom;

means associated with said housing for delivering said outletted liquid to a point of use;

pumping means included within said housing for enforcing flow of said liquid from said permitting means to said outletting means;

a well defined in a wall of said housing;

a pair of electrical contacts exposed through the wall of said well and spaced apart longitudinally of said well;

a barrel slideably disposed within said well and having one end portion projecting outwardly from said well;

an elongated resilient electrically-conductive element secured on the lower end portion of said barrel in alignment with said contacts and of a conformation to electrically bridge said contacts when said barrel is moved to a first position but to open said bridge when said barrel is moved to a second position;

an operator secured to said one end portion;

a first spring disposed with respect to said barrel to urge said barrel to said first position but yieldable in response to pressure exerted on said operator to move said barrel into said second position;

a finger pivotally connected at one end to said operator to enable said finger to swing laterally;

a second spring disposed with respect to said operator to urge said finger to swing only in a first direction;

means defining a raceway having first and second ramps and a notch therebetween;

means including a pin projecting from the other end of said finger into said raceway for enabling travel of said pin out of said notch into said first ramp under urging of said second spring and with pressure applied to said operation followed by movement of said barrel outwardly of said well under urging of said first spring and thereafter enabling renewed pressure applied to said operator to effect travel of said pin along said second ramp and return of said pin into said notch.

7. An electrical switch comprising:

a housing defining an interior closed compartment;

means defining a well in a wall of said housing;

a pair of electrical contacts exposed through the wall of said well and spaced apart longitudinally of said well;

a barrel slideably disposed within said well and having one end portion projecting outwardly from said well;

an elongated resilient electrically-conductive element secured on the lower end portion of said barrel in alignment with said contacts and of a conformation to electrically bridge said contacts when said barrel is moved to a first position but to open said bridge when said barrel is moved to a second position;

an operator secured to said one end portion;

a first spring disposed with respect to said barrel to urge said barrel to said first position but yieldable in response to pressure exerted on said operator to move said barrel into said second position;

a finger pivotally connected at one end to said operator to enable said finger to swing laterally;

a second spring disposed with respect to said operator to urge said finger to swing only in a first direction;

means defining a raceway having first and second ramps and a notch therebetween;

means including a pin projecting from the other end of said finger into said raceway for enabling travel of said pin out of said notch into said first ramp under urging of said second spring and with pressure applied to said operation followed by movement of said barrel outwardly of said well under urging of said first spring and thereafter enabling renewed pressure applied to said operator to effect travel of said pin along said second ramp and return of said pin into said notch.

8. An electrical switch as defined in claim 7 and which further includes an hermetic seal disposed between the outer wall of said barrel and the inner wall of said well.

9. An irrigation appliance comprising:

a reservoir for containing a supply of liquid;

a pump coupled to said reservoir for receiving liquid therefrom and pressuring increased flow of said liquid from said reservoir through said pump;

a device physically located remotely from but coupled to said pump for receiving said liquid from said pump and serving to deliver said liquid toward a point of use;

means included within said device for adjustably throttling the rate of flow of said liquid through said device;

governing means located in the path of flow of said liquid through said pump from said reservoir to said device and including first and second flow regulators;

said first regulator responsive to pump suction for enabling liquid flow from said reservoir at a rate determined in response to adjustment of said throttling means and said second regulator responsive to pump pressure for enabling liquid flow from said pump back to said reservoir at a rate correspondingly determined by adjustment of said throttling means;

said device being a hand-held unit including a central bore through which said liquid flows, which includes a valve moveable within said bore to throttle flow therethrough and which includes a finger-operable control for adjusting movement of said valve with said valve being rotationally moveable to variably throttle said flow and also being moveable in a direction lateral to said bore for blocking said flow.

10. An irrigation appliance comprising:
a reservoir for containing a supply of liquid;
a pump coupled to said reservoir for receiving liquid therefrom and pressurizing increased flow of said liquid from said reservoir through said pump;
a device physically located remotely from but coupled to said pump for receiving said liquid from said pump and serving to deliver said liquid toward a point of use;
means included within said device for adjustably throttling the rate of flow of said liquid through said device;
governing means located in the path of flow of said liquid through said pump from said reservoir to said device and including first and second flow regulators;
said first regulator responsive to pump suction for enabling liquid flow from said reservoir at a rate determined in response to adjustment of said throttling means and said second regulator responsive to pump pressure for enabling liquid flow from said pump back to said reservoir at a rate correspondingly determined by adjustment of said throttling means;
said first regulator including a first check valve poled to normally pass liquid during pump suction and said second regulator being a second check valve resiliently urged to permit reverse flow back to said reservoir during pump pressure only on reduction of flow by said throttling and with said first check valve including a cylinder having an internal bore within which said second check valve is located.

11. An irrigation appliance comprising:
a reservoir for containing a supply of liquid;
a pump coupled to said reservoir for receiving liquid therefrom and pressurizing increased flow of said liquid from said reservoir through said pump;
a device physically located remotely from but coupled to said pump for receiving said liquid from said pump and serving to deliver said liquid toward a point of use;
means included within said device for adjustably throttling the rate of flow of said liquid through said device;
governing means located in the path of flow of said liquid through said pump from said reservoir to said device and including first and second flow regulators;
said first regulator responsive to pump suction for enabling liquid flow from said reservoir at a rate determined in response to adjustment of said throttling means and said second regulator responsive to pump pressure for enabling liquid flow from said pump back to said reservoir at a rate correspondingly determined by adjustment of said throttling means;
said first regulator including a first check valve poled to normally pass liquid during pump suction and said second regulator being a second check valve resiliently urged to permit reverse flow back to said reservoir during pump pressure only on reduction of flow by said throttling and with said first check valve being free floating in the path of liquid flow between said pump and said reservoir.

12. An irrigation appliance comprising:
a reservoir for containing a supply of liquid;
a pump coupled to said reservoir for receiving liquid therefrom and pressurizing increased flow of said liquid from said reservoir through said pump;
a device physically located remotely from but coupled to said pump for receiving said liquid from said pump and serving to deliver said liquid toward a point of use;
means included within said device for adjustably throttling the rate of flow of said liquid through said device;
governing means located in the path of flow of said liquid through said pump from said reservoir to said device and including first and second flow regulators;
said first regulator responsive to pump suction for enabling liquid flow from said reservoir at a rate determined in response to adjustment of said throttling means and said second regulator responsive to pump pressure for enabling liquid flow from said pump back to said reservoir at a rate correspondingly determined by adjustment of said throttling means;
said first regulator including a first check valve poled to normally pass liquid during pump suction and said second regulator being a second check valve resiliently urged to permit reverse flow back to said reservoir during pump pressure only on reduction of flow by said throttling and with said first check valve including an unidirectional flow opening formed within the body of said second check valve.

13. An irrigation appliance comprising:
a housing having a top wall and a bottom wall joined to said top wall by a circumferential side wall;
a cover having a normally horizontal wall from which laterally projects a circumscribing wall shaped to mate with said side wall when said cover is positioned to overlie said housing in enveloping relationship;
inlet means defining an opening in said top wall;
outlet means defining an opening in said horizontal wall and so located as to be in alignment with said inlet means when said cover is inverted to dispose said circumscribing wall normally upstanding from said horizontal wall;
a valve of generally I-shaped longitudinal cross section composed entirely of resilient material and disposed with its single central leg within said opening in said horizontal wall, said valve having one transverse bar at one end of said leg with said bar having a marginal portion projecting outwardly from said leg to overlie and seal said opening in said horizontal wall when urged downwardly in normal use;
means disposed within said inlet opening for engaging another transverse bar at the other end of said leg and urging said valve in a direction disengaging the sealing of said opening;
and outletting means coupled to said housing for delivering liquid from said inlet to a point of use when said valve is opened.

14. An irrigation appliance as defined in claim 13 in which said transverse bars are in the form of flanges and have outer marginal portions projecting outwardly from said central leg, each of said marginal portions, when unflexed, drooping toward the other marginal portion at the other end of said valve.

15. An irrigation appliance as defined in claim 14 in which the marginal portion of said bar at said one end overlies a portion of the horizontal wall inner surface around said opening in said horizontal wall.

16. An irrigation appliance as defined in claim 14 in which said flanges are circumferentially continuous.

17. An irrigation appliance as defined in claim 14 in which said inlet means is defined by a well in said top wall with said well having an outlet passage, said means disposed within said inlet comprises a nub formed around said outlet passage with the outer surface of said other bar being engageable with said nub and with said nub having passages therein to provide fluid communication between said well and said outlet passage when said other bar is in engagement with said nub.

18. An irrigation appliance as defined in claim 17 in which in the open position of said valve an inner surface of said other bar engages stop means formed around the outlet opening in the outer surface of said horizontal wall with there being passages in said stop means providing fluid communication past said other bar between said outlet opening and said nub passages when said other bar is in engagement with said nub.

19. An irrigation appliance comprising:
a reservoir for containing a supply of liquid;
a pump having an inlet and an outlet with said inlet being coupled to said reservoir for receiving liquid therefrom and pressurizing increased flow of said liquid from said reservoir through said outlet;
a device for receiving said liquid from said pump and serving to deliver said liquid toward a point of use;
a single hose coupling said outlet to said device;
means included within said device for adjustably throttling the rate of flow of said liquid through said device;
governing means located in the path of flow of said liquid through said pump from said reservoir to said said device and including first and second flow regulators;
said first regulator being responsive to pump suction for enabling liquid flow from said reservoir at a rate through said first regulator determined in response to adjustment of said throttling means and said second regulator being responsive to pump pressure for enabling liquid flow from said device back through said hose to said reservoir at a rate correspondingly determined by adjustment of said throttling means.

20. An irrigation appliance as defined in claim 19 in which said device is physically located remotely from said pump.

21. An irrigation appliance as defined in claim 19 in which both of said first and second regulators are located on the suction side of said pump between said reservoir and said pump.

22. An irrigation appliance as defined in claim 19 in which device is a hand-held unit including a central bore through which said liquid flows, which includes a valve moveable within said bore to throttle flow therethrough and which includes a finger-operable control for adjusting movement of said valve.

23. An irrigation appliance as defined in claim 22 in which said valve is rotionally moveable to variably throttle said flow and also is moveable in a direction lateral to said bore for blocking said flow.

24. An irrigation appliance as defined in claim 19 in which said first regulator includes a first check valve poled to normally pass liquid during pump suction and said second regulator is a second check valve resiliently urged to prevent reverse flow back to said reservoir during pump pressure only upon reduction of flow by said throttling.

25. An irrigation appliance as defined in claim 24 in which both of said first and second check valves are ball valves.

26. An irrigation appliance as defined in claim 24 in which said first check valve includes a cylinder having a internal bore within which second check valve is located.

27. An irrigation appliance as defined in claim 24 in which said first check valve is free floating in the path of liquid flow between said pump and said reservoir.

28. An irrigation appliance as defined in claim 24 in which said first check valve includes a unidirectional flow opening formed within the body of said second check valve.

* * * * *

UNITED STATES PATENT OFFICE
CERTIFICATE OF CORRECTION

Patent No. 4,989,590                    Dated Feb. 5, 1991

Inventor(s) John Baum, Gary Thomas and James Hickman

It is certified that error appears in the above-identified patent and that said Letters Patent is hereby corrected as shown below:

Column 5, line 58:  "a" should read -- the --.

Column 8, line 23:  "disposed" should read -- dispose --.

Column 14, line 28:  "prevent" should read -- permit --.

Column 14, line 36:  "a" should read -- an --.

Signed and Sealed this

Twenty-first Day of April, 1992

Attest:

HARRY F. MANBECK, JR.

*Attesting Officer*    *Commissioner of Patents and Trademarks*